United States Patent
Bray

(10) Patent No.: US 6,477,473 B2
(45) Date of Patent: Nov. 5, 2002

(54) ULTRASONIC STRESS MEASUREMENT USING THE CRITICALLY REFRACTED LONGITUDINAL ($L_{CR}$) ULTRASONIC TECHNIQUE

(76) Inventor: Don E. Bray, 1601 Fontaine St., College Station, TX (US) 77842-0315

( * ) Notice: Subject to any disclaimer, the term of this patent is extended or adjusted under 35 U.S.C. 154(b) by 0 days.

(21) Appl. No.: 09/898,218

(22) Filed: Jul. 3, 2001

(65) Prior Publication Data

US 2001/0049587 A1 Dec. 6, 2001

Related U.S. Application Data

(62) Division of application No. 09/234,157, filed on Jan. 19, 1999.
(60) Provisional application No. 60/094,684, filed on Jul. 30, 1998.

(51) Int. Cl.[7] ............... G01L 1/00; G01L 3/00; G01L 5/00
(52) U.S. Cl. ........................... 702/42; 73/760
(58) Field of Search ............... 702/39, 42, 35, 702/59, 171, 185, 54; 73/597, 579, 640, 642, 788, 841, 866.5, 432.1, 632, 862.041–862.046, 819, 766

(56) References Cited

U.S. PATENT DOCUMENTS

| | | | |
|---|---|---|---|
| 3,720,098 A | | 3/1973 | Dixon |
| 3,812,709 A | * | 5/1974 | Benson et al. ............... 73/597 |
| 4,398,421 A | * | 8/1983 | White ............... 73/597 |
| 4,413,517 A | | 11/1983 | Soden |
| 4,453,410 A | | 6/1984 | Schmitz et al. |
| 4,458,534 A | * | 7/1984 | Kissing ............... 73/642 |
| 4,474,064 A | | 10/1984 | Naruse et al. |
| 4,484,475 A | * | 11/1984 | Ogura et al. ............... 73/579 |
| 4,522,071 A | * | 6/1985 | Thompson ............... 73/597 |
| 4,543,649 A | * | 9/1985 | Head et al. ............... 367/96 |
| 4,577,507 A | | 3/1986 | Jestrich et al. |
| 4,926,692 A | | 5/1990 | Brokowski et al. |
| 5,007,291 A | * | 4/1991 | Walters et al. ............... 73/640 |
| 5,016,200 A | | 5/1991 | Passarelli |
| 5,020,378 A | * | 6/1991 | Hesthamer et al. ............... 73/779 |
| 5,085,082 A | * | 2/1992 | Cantor et al. ............... 73/622 |
| 5,170,366 A | * | 12/1992 | Passarelli ............... 702/41 |
| 5,289,387 A | * | 2/1994 | Higo et al. ............... 702/42 |
| 5,299,458 A | * | 4/1994 | Clark, Jr. et al. ............... 73/597 |
| 5,503,020 A | | 4/1996 | Mandracchia |
| 5,951,163 A | * | 9/1999 | Jen et al. ............... 374/119 |

OTHER PUBLICATIONS

Hartford Steam Boiler Co., "The Hartford Wedge," (Aug. 21, 1982).
Hartford Steam Boiler Co., "The Hartford Wedge System for Dryer Roll Thickness Measurements."
Stanley, Rod K., Nondestructive Evaluation, Revised Edition, Jan. 1997, CRC Press, Boca Raton, FL, U.S.A.
King, R.R., Birdwell, J.A., Clotfelter, W.N., Risch, E.R., and Bray, D.E., "Improved Methods for Nondestructive Measuring Residual Stress in Railway Wheels," Apr. 1973, pp. 91–105, Proceedings of the Ninth Symposium on NDE, San Antonio, TX.

(List continued on next page.)

Primary Examiner—John S. Hilten
Assistant Examiner—Demetrius Pretlow
(74) Attorney, Agent, or Firm—Carstens Yee & Cahoon LLP; David W Carstens

(57) ABSTRACT

The latent stress in a material can be measured using critically refracted longitudinal ultrasonic technique. The system uses a frame to hold a hydraulic piston. The piston is used to apply an adjustable force against the probes. A signal is initiated by a first transducer. The signal is angled against the piece under test so as to create a critically refracted wave along the piece. The delay time to receive the wave at a first and second probe is measured. The delay time correlates to a stress in the piece.

10 Claims, 4 Drawing Sheets

OTHER PUBLICATIONS

Srinivasan, M., Bray, E.D., Junghans, P., and Alagarsamy, A., "Critically Refracted Longitudinal Waves Techniquie: A New Tool for the Measurement of Residual Stresses in Castings," AFS (American Foundryman Society) Transactions, 1991, pp. 265–267, vol. 91.

Bray, Don E., Kim, S–J., and Fernandes, M., "Ultrasonic Stress Measurement in Aluminum Plates," Proceedings Ninth International Symposium on Nondestructive Characterization of Materials, Jun. 28–Jul. 2, 1999, Sydney, Australia.

Bray, Don E., and Chance, Brent, "Practical Aspects of Ultrasonic Stress Measurement," Proceedings 1999 AME NDE Engineering division Topical Conference, Apr. 20–22, 1999, San Antonio, TX.

Bray, Don E., Tang, Wei, Tittman, Bernard, and Miyasaka, Chiaki, "Detecting Load Damage in Composite Materials using Ultrasonic Techniques," Proceedings 1999 ASME NDE Engineering Division Topical Conference, Apr. 20–22, 1999, San Antonio, TX.

Bray, Don E., "Ultrasonic Stress Measurement in Turbine Components," Proceedings of the 1998 International Joint Power Generation Conference—Power, Aug. 23–26, 1998, pp. 43–50, vol. 2, J. Legler, Ed., PWR—vol. 33, The American Society of Mechanical Engineers, Baltimore, MD.

Bray, Don E. and Srinivasan, M.N., "Near–Surface Through–Thickness Residual Stress Evaluation in Ductile Iron Using the Critically Refracted Longitudinal Wave Technique," Presented at the ASME–ASIA '97 Congress & Exhibition, Sep. 30–Oct. 2, 1997 Paper No. 97–AA–68, Singapore.

Bray, Don E. and Dietrich, M., "Stress Evaluation in High Speed Rotation Machinery with the LCR Ultrasonic Technique," Proceedings of the 26th Turbo Machinery Symposium, Bailey, Jean C., Tech. Ed., Sep. 16–18, 1997, pp. 143–149, Texas A&M University, College Station, TX, USA.

Bray, Don E., and Tang, W., "Evaluating Stress Gradients in Steel Plates and Bars with the LCR Ultrasonic Wave," Approximate Methods in the Design and Analysis of Pressure Vessels and Piping Components, Proceedings 1997 ASME Pressure Vessels and Pipinh Conference.

Tang, W., and Bray, D.E., "Stress and Yielding Studies Using Critically Refracted Longitudinal Waves," NDE Engineering Codes and Standards and Material Characterization, Proceedings 1996 ASME Pressure Vessels Piping Conference, Montreal, PQ, Jul. 1996, pp. 41–48, PVP—vol. 322.

Chundu, S., Srinivasan, M., and Bray, D., "Residual Stress Measurement in Ductile Cast Iron Using the LCR Ultrasonic Technique," NDE: Apllications, Advanced Methods, Codes and Standards, PVP—vol. 216, NDE vol. 9, Jun. 1991, pp. 49–54, Proceedings 1991 PVP Conference, San Diego, CA.

Leon–Slamanca, T., Reinhar, E., Bray, D.E., and Golis, M., "Field Applications of an Ultrasonic Method for Stress Meausrement in Structure," Apr. 1989, pp. 1484–1489, Boogaard, J. and Van Dijk, G., eds, Nondestuctive Testing (Proceedings 12th World Conference). Apr. 1989.

Bray, D.E., and Egle, D.M., "Field Tests on the Use of Ultrasonic Wave Velocity Changes to Detect Longitudinal Stress Variations in Railroad Rail," Conference on Nondestructive Techniques for Measuring the Longitudinal Force in Rails, Feb. 1979, FRA/ORD–80/50.

Bray, D.E., "Measurement of Longitudinal Stresses in Railroad Rails by Acoustic Wave Velocity," Proceedings of a workshop in Nondestructive Evaluation of Residual Stress. NTIAC–76–2, 1975, pp. 187–195, Nondestructive Testing Information Analysis Center, San Antonio, TX.

Bray, Don E., "Fizing the Impendance Mismatch in US Technical Education," Mehl Honor Lecture, Keynote Address, Fall Conference, Oct. 11–19, 1999, The American Society for Nondestructive Testing, Phoenix, AZ.

Bray, Don E., "Application of Ultrasonic Stress Measurement to Engineering Components," Pres. No. 2Ae3, Invited presentation to 134th Meeting of the Acoustical Society of American, Dec. 2, 1997, San Diego, CA.

Leon–Slamanca, T., and Bray, D.E., "Residual Stress Measurement in Steel Plates and Welds Using Critically Refracted Longitudinal (Lcr) Waves," Research in Nondestructive Evaluation, Springer–Verlag (New York), p. 169–184, Apr. 21, 1996.

Malur N. Srinivasan, Srinicasulu N. Chundu, Don E. Bran, and A. Alagarsamy, Ultrasonic Technique for Residual Stress Measurement in Ductile Iron Continuous Cast Round Bars, Journal of Testing and Evaluation, JTEVA, vol. 20 (No. 5), p. 331–335, Sep. 21, 1992.

Nisar Shaikh, "Transducers and Technique for Ultrasonic Nondestructive Evaluation of Structural Plastics," Review of Progress in Quantitative Nondestructive Evaluation, Plenum Press, New York, pp. 1831–1835, Apr. 21, 1992.

Egle, D.M. and Bray, D.E., "Application of the Acousto–elastic Effect to Rail Stress Measurement," Materials Evaluation, Mar. 21, 1979.

Egle, D.M., and Bray, D.E., "Nondestructive Measurement of Longitudinal Rail Stresses; Application of the Acoustoelastic Effect to Rail Stress Measurement," DOT Report FRA/ORD–77/34.I., 113 pages, Jan. 21, 1978.

Moskal, Max D., "Round Robin Evaluation of Gray Cast Iron Thickness Test Methods," TAPPI Proceedings, 1990 Engineering Conference, Seattle, WA, Sep. 24–27, 1990.

White, Dennis, "Examining Cast Iron Dryers and Determining Tensile Strength," TAPPI Proceedings, 1992 Engineering Conference, USA, 1992.

Pfluger, R., Bran, D.E., and Srinivasan, M., "Evaluation of Residual Stress Gradients in Ductile Cast Iron Using the Critically Refracted Longitudnal (Lcr) Wave Technique," Proceedings, International Chemical and Petroleum Industry Inspection Technology IV Topical Conference, Houston, TX Jun. 19–22, 1995, pp. 255–258.

* cited by examiner

ULTRASONIC STRESS MEASUREMENT USING THE CRITICALLY REFRACTED LONGITUDINAL ($L_{CR}$) ULTRASONIC TECHNIQUE

This application is a division of U.S. Ser. No. 09/234,157, filed Jan. 19, 1999 and claims benefit of Provisional Serial No. 60/094,684 filed Jul. 30, 1998.

BACKGROUND OF THE INVENTION

1. Technical Field

The present invention relates to an apparatus and method for non-destructive testing of stress within solid materials using the $L_{CR}$ ultrasonic technique. The improved technique and apparatus provides a more accurate measurement.

2. Description of the Related Art

The non-destructive testing for stress in metals has long been recognized as an important method for evaluating metal components to predict both the failure location and rate, to identify stressed components prior to failure, and many other safety related considerations. Non-destructive testing is used extensively in a wide variety of industries including the aviation, automotive, petroleum, and chemical industries, and various construction and structural related fields. The use of non-destructive testing on specific components ranges from the testing of steel turbine blades in jet engines to steel support beams in bridges and other large structures. The benefit of non-destructive testing is self-evident. Components in use can be tested to determine the stress levels in the components without destroying the components.

Techniques such as x-ray diffraction and Barkhausen noise analysis have been successfully applied for nondestructive stress measurements. While the x-ray techniques are quite reliable in their measurements, they measure stress in only the top few angstroms of the surface, and the results may not be indicative of internal stresses. The Barkhausen method is based on small changes in magnetic permeability due to stress. Application of the Barkhausen method is limited to electrical conducting materials. It has been available for a number of years, and has not been shown to give generally reliable results.

The $L_{CR}$ ultrasonic technique indicates stress through the acoustoelastic principle where small variations in strain affect the wave speed. By measuring the wave speed (or travel-time between known points) the change in stress can be calculated. Other material variations such as texture and temperature also affect the travel-time. The investigator using the $L_{CR}$ method must be aware of these other effects so that the best data indicative of stress variation is obtained.

The relationship of measured $L_{CR}$ wave travel-time change and the corresponding uniaxial stress is given by:

$$\Delta\sigma = \frac{E}{Lt_0}(t - t_0 - \Delta t_T)$$

where $\Delta\sigma$ is change in stress, E is Young's modulus, and L is the acoustoelastic constant for longitudinal waves propagating in the direction of the applied stress field, as given in Table 1. Travel-time change ($\Delta t$) is the measured travel-time (t) minus the reference travel-time ($t_0$). The reference travel-time $t_0$ is a property of the probe sensor spacing for an assumed stress free material.

TABLE 1

Typical values for acoustoelastic constant (L)

| Material | Load | L |
|---|---|---|
| Pearlitic steel | Tension | −2.38 |
|  | Compression | −2.45 |
| 4140 steel | Tension 2.25 MHz | −2.2 |
|  | Tension 5 MHz | −2.36 |
| Clear acrylic - aircraft grade | Tension | −2.14 |

Temperature induced speed changes occur both in the material being investigated and in the probe material. The relationship of wave speed and temperature (dc/dT) is given by:

$$\frac{dc}{dT} = k_T \frac{m}{s - °C.}$$

where $k_T$ is the constant for a particular material, as given in Table 2.

TABLE 2

Temperature effects on wave speed

| Material | $k_T$ |
|---|---|
| PMMA | −2.3 |
| Pearlitic Steel | −0.55 |

The effect of temperature on travel-time will be $$\Delta t_T = \frac{d}{k_T \Delta T}$$

where d is the travel distance in the material and $\Delta T$ is the measured temperature change. Obviously, the temperature effect for the PMMA wedge material is greater than that of the steel. Where data are collected under moderately uniform temperature conditions, the temperature effect, $\Delta t$, can be ignored. For large temperature variations, the temperature of the wedge can be monitored with a thermocouple. The distance of wave travel in the wedge can be measured and a suitable correction in the travel-time can be made.

Texture as typically encountered in cold-rolled plates and other structural shapes can have a significant affect on the wave speed. While the affect of texture on the $L_{CR}$ wave speed is less than that encountered by the shear waves often used in acoustic-birefringence stress measurements, there still is concern about the effects.

Special data collection procedures may be used to minimize the effects of texture. In many items where stress is a concern, the texture may be uniform throughout. In these cases, $L_{CR}$ travel-times taken with the probe always at the same orientation relative to the geometry of the item may be free of texture variation. In this case, the major effect may be stress. This has been found to be true for plates and welded plates. However, there is a need for more data on additional structures and shapes before this assumption may be more widely made.

Ideally, the $L_{CR}$ pulse is a true, nondispersive wave travelling at the longitudinal wave speed of the material. There are shape and material effects, however, that can cause dispersion of the wave. In many of these cases, the wave can still be used for stress measurement by the careful operator, and by choosing the proper probe.

Wave-guide effects are one of the most serious causes of dispersion. These occur in plates and pipes when the wavelength of the wave approaches some fraction of the thickness. Typically, when the ratio of plate thickness to wavelength is ten or above, there is no risk of any waveguide effect. Satisfactory results have been obtained with ratios of five, however. Texture effects, discussed above, and grain boundary scattering also affects the pulse shape. Waveguide effects are the easiest to eliminate due to knowledge of the geometry. Texture may be evaluated with a contact shear wave acting across the thickness. Grain boundary scattering may be evaluated with attenuation measurements also across the boundary. There are no data yet on acceptable ranges for $L_{CR}$ stress measurement, however.

Choosing the proper reference location within the $L_{CR}$ pulse can enable the collection of reliable data. Typically, the second positive zero crossing at the first arrival of the pulse is used as this reference. In nondispersive conditions, this location is easy to identify at all pulse arrivals. Under dispersive conditions, however, identification may be more difficult. In difficult circumstances, identification can be aided by sliding a receiver probe along the travel path and observing the change of shape.

Ultrasonic stress measurement techniques have been developed in the past. Some use longitudinal waves, but they have not met with success due to the absence of a method for accurately controlling the coupling state between the probe and the item being inspected. Others use shear (SH) and/or Rayleigh waves which are well known to be less sensitive to stress than is the $L_{CR}$ wave. Other significant workers in the field of ultrasonic stress measurement include R. B. Thompson at Iowa State University, Eckhardt Schneider at the Fraunhofer Institute in Saarbrucken, Germany, Teodore Leon-Salamanca and Eugene Reinhart at Reinhart and Associates in Austin, Tex. and Ray Schramm and Van Clark at the National Institute for Science and Technology in Boulder, Colo.

Accordingly, a need exists for a non-destructive testing method and apparatus to accurately indicate the internal stresses of metal. The method and apparatus should accurately control the coupling state between the probe and the item being inspected and take into account or avoid various interference factors, thus providing accurate and reliable stress measurements.

SUMMARY OF THE INVENTION

The $L_{CR}$ ultrasonic technique is a unique nondestructive method for evaluating stress levels and other mechanical property variations in engineering components, structures and materials. The inspection is accomplished with a newly designed apparatus incorporating an $L_{CR}$ ultrasonic probe, a variable force application device and a mechanism for attachment of the probe to the item being evaluated.

The new feature of the $L_{CR}$ technique is the ability to apply an even, linear variable force to the interface of the $L_{CR}$ probe and the item being inspected. The force is equal at the interfaces of the two or more receiving probes since the single force applicator is located equidistant between the interfaces. Further, the magnitude of the force can be established through the use of a measurement device such as a pressure gauge. This feature enables the reliable and repeatable measurement of 0.0004% or better on the $L_{CR}$ travel-time changes. The $L_{CR}$ probe operates in a send-receive mode, using one transmitter (T) and either one or more receivers (R1 and/or Rn). Both the send and receiving probes are on one side of the material. The $L_{CR}$ wave is excited at approximately the first critical angle +/−2 degrees for the wedge and material combination. The pulse travels from the transmitter to the receivers as a bulk critically refracted longitudinal ($L_{CR}$) wave and encounters the stress effect in its path. Since the $L_{CR}$ wave propagation is just beneath the surface, the stress and other material property variations within its penetration path affect the speed. Also, surface conditions have little affect on the wave travel. Moreover, frequency variation and analysis techniques may establish stress and other property gradients existing below the surface.

The $L_{CR}$ stress measurement process has been demonstrated in lab and field applications in railroad rail, welded steel plates, a turbine disk, a compressor rotor, rolled aluminum plates, rolled steel plates, titanium plates and ductile cast iron samples. A prototype $L_{CR}$ stress measurement apparatus has been developed and demonstrated.

Generally speaking, the requirement for the contact area during the inspection is that it must be free of dirt, water, oil, scale and other loose debris that can affect the probe contact. Ordinary metal scale does not affect the $L_{CR}$ data, provided that it is tightly adhered to the plate or pipe. Ultrasonic instrumentation preferable for collecting $L_{CR}$ data are a typical commercial pulser/receiver and a computer data acquisition system with a high speed digitizing board, or a digital oscilloscope. Arrival time resolution of 0.1 ns or better is preferable for the instrumentation. The board and suitable software can be conveniently fitted into expansion slots on a PC or Laptop computer. Since temperature can affect the travel-time data, these data also may be collected during the test. Stress changes may then be calculated from the arrival times, using the appropriate formulas.

Judgement of stress change or stress fields would be based on the deviation of the observed travel time from some previously established zero stress norm. The zero stress norms may be established with prior data on the material being inspected, or on comparison with a known stress free region in the material. The distinct advantage of the $L_{CR}$ ultrasonic technique used by the apparatus described here is that the frame and force application feature enables the accurate collection of travel-time data. These data will enable the establishment of stress variations in the plane of the plate or pipe, and with depth.

The above, as well as additional features and advantages of the present invention will become apparent in the following written detailed description.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE DRAWINGS

Typical stress induced travel-time changes are small, at approximately 0.01%. Thus, travel-time variations caused by the testing procedure must be reduced to at least one tenth of that level for the desired stress resolution. Testing procedure variations can arise from the instrumentation and the repeatability of the ultrasonic probe system. Instrumentation capable of measuring arrival times of a least a nanosecond is needed for good resolution. Further, probe repeatability at a designated location should be in the 2 to 3 ns range.

Figure 1:
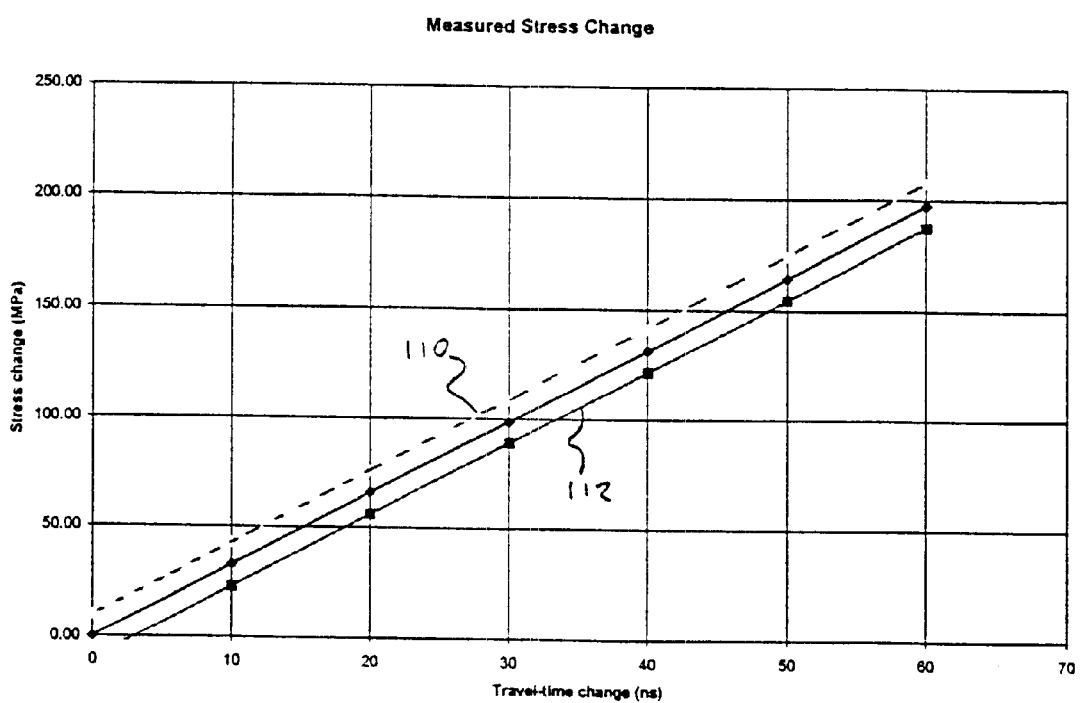
FIG. 1 illustrates the typical relationship of stress change with travel-time change for steel. Outer lines show variations with ±3 ns system repeatability.

For reference purposes, the nominal relationship of stress variation and travel-time for steel is shown in FIG. 1. The outer lines 110, 112 show the range for an expected measurement variation of ±3 ns.

Figure 2A:
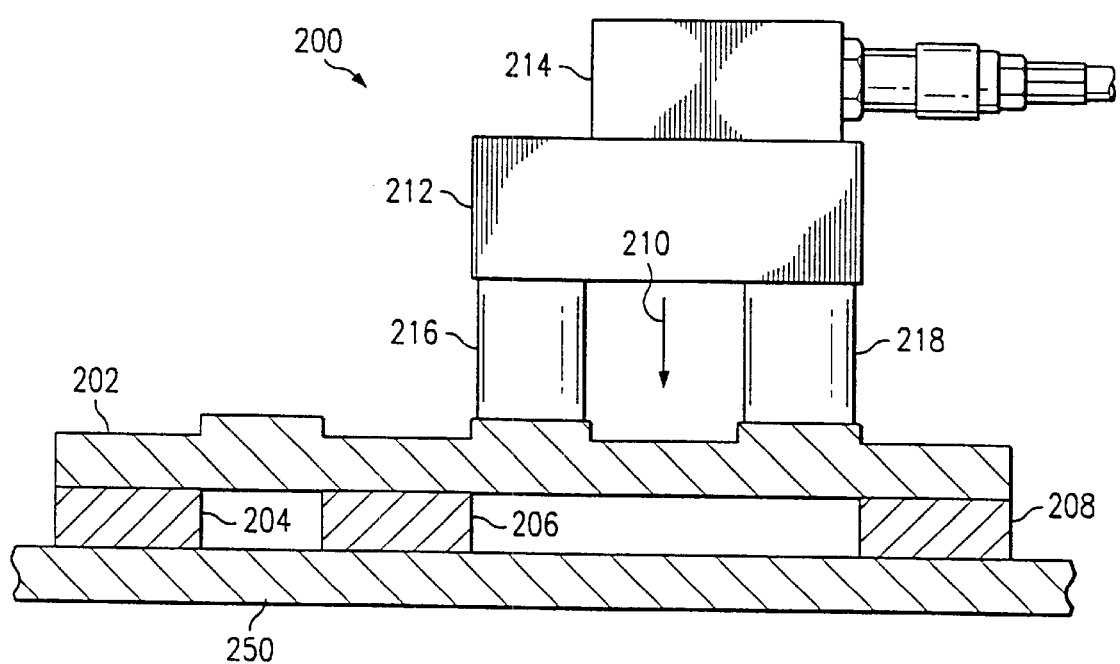
FIG. 2a is a schematic of a probe frame of one embodiment of the invention.

One distinguishing feature of the $L_{CR}$ technique of the present invention is the ability to apply an even, linear variable force to the interface of the $L_{CR}$ probe and the item being inspected. The force is equal at the interfaces of the two receiving probes, or single receiving probe and transducer, since the single force applicator is located equidistant between interfaces. This is illustrated in FIG. 2a. A probe assembly 200 is shown comprising a rigid member or probe frame 202 which is constructed of a rigid material such as aluminum, steel or a ceramic, a transducer 204 which initiates the signal through the test sample 250, and two receiving probes 206, 208. A force 210 is applied at a point equidistant between the two receiving probes 206, 208.

Figure 2B:
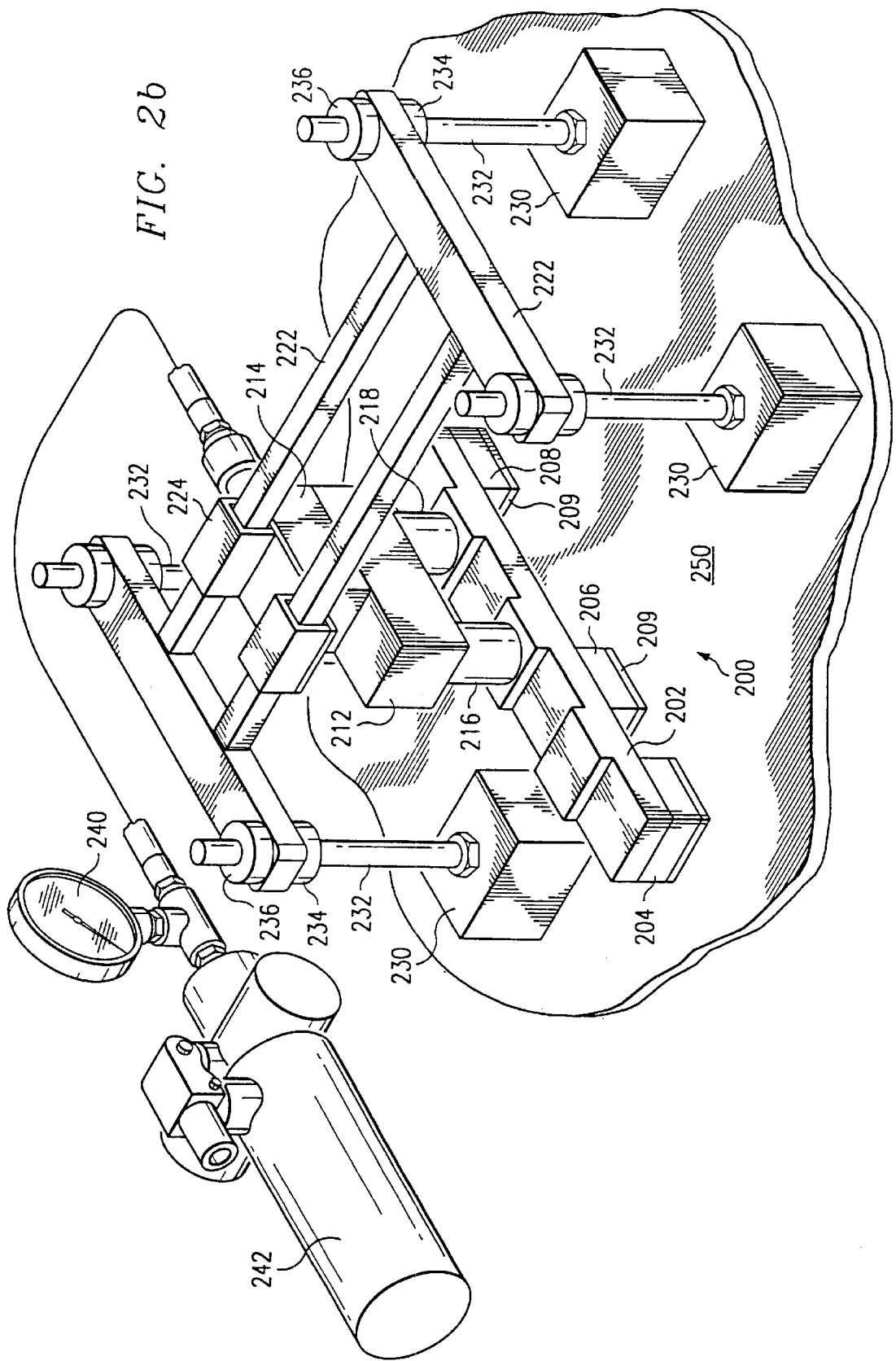
FIG. 2b is a perspective view of one apparatus embodiment of the invention; and, FIG. 3 is a schematic of the data collecting system of one embodiment of the invention.

FIG. 2b shows one embodiment of the entire assembly for the invention. Again, shown is the probe assembly 200 comprising an aluminum probe frame 202, a transducer 204, and two receiving probes 206, 208. At the contact between the receiving probes 206, 208, and the surface of the tested material 250 is shown polystyrene pads 209 which are preferable due to their ultrasonic properties. The force 210 illustrated in FIG. 2a is transmitted to the probe assembly by way of a hydraulic piston or ram 214, which is driven by a hydraulic pump 242. This piston 214 is shown in FIG. 2a connected to a rigid block 212. The rigid block 212 is placed over two rigid posts 216, 218, which transmit the force 210 to the aluminum probe frame 202. The piston 214 in turn abuts and transmits an opposite force to the load frame 222, comprised of various support members, by way of a sliding plate bracket 224 or other connecting means. Alternatively, the piston 214 can be attached to the sliding plate bracket 224 and be physically placed on top of the rigid block 212. The load frame 222 is secured to four posts 232 by upper collars 236 and lower collars 234. These four posts 232 are attached to four magnets 230 (three of which are shown), which secure the entire assembly to the test sample 250.

The load frame 222 shown in FIG. 2b is designed to use magnets 230 for force attraction to steel samples. Other devises such as vacuum and mechanical constraints can be used. Such devices are necessary when the test sample 250 is, for example, aluminum, ceramic, or of an unusual geometry for which a magnetic interface would not be possible or appropriate.

The hydraulic ram 214 is fitted on the top of the probe frame 200 to provide a variable force at the couplant interface between the probes 206, 208 and the test sample 250. The force line 210 of the ram 214 is midway between the two receiving probes 206, 208 (also referred to herein as R1 and R2), giving uniform pressure on these two interfaces. Pressure on the ram 214 is indicated by a pressure gauge 240 on a hydraulic pump 242. The hydraulic pump 242 can also be mounted directly on the sliding plate bracket 224.

Obtaining the higher pressures required for achieving small travel-time variations is dependent on good magnetic coupling or other suitable interface. This requires that the magnets 230 be firmly placed on the plate or sample 250, and that the load frame 222 be able to move freely on the posts 232. If this condition is not met, the magnets 230 will pull loose from the plate when the piston force is applied. Some adjustment of the magnet 230 position and the collar 234, 236 placement is often needed to achieve good quality data.

A typical setup for one embodiment of the invention involves first positioning the lower collars 234 on the posts 232 so that the tops of the collars 234 are about 159 mm (6.25 in.) from the plate 250. Next, the load frame 222 is placed on the posts 232 and the upper collars 236 are secured leaving about 1 mm of clearance between the upper collar 236 and the frame 222. The entire assembly is then placed in position on the plate 250 and the magnets 230 are activated. After assuring that the contact areas on the probes 206, 208 and the plate 250 are clean, couplant is applied to the probe contact areas. The probe assembly 200 is then inserted and the sliding plate bracket 224 is positioned over the ram 214. Hydraulic pressure is then applied via the hydraulic pump 242 in order to secure the probe assembly 200 in place. The higher the pressure achieved the more accurate are the results. However, accurate results have been obtained using the embodiment illustrated in the range of 200 to 400 psi.

The embodiment illustrated in FIGS. 2a and 2b shows a single transducer 204 and two receiving probes 206, 208. Use of two receiving probes 206, 208 allows for elimination of the temperature effects on the stress measurements. In applications where temperature effects are nominal, the same principals of the invention can be applied by using a single transducer and a single receiving probe, with a force applied equidistant between the two.

Further, while the embodiment illustrated in FIGS. 2a and 2b illustrate an embodiment of the invention used for testing a flat, steel plate as the test material 250, it is understood that modifications in this embodiment can be made in order to adapt the principals of the invention to a wide variety of test materials 250. For example, the invention has been demonstrated using a similar embodiment on a much smaller scale in order to test titanium plates measuring 3 inches by 3 inches. Also, clamps and minor adjustments to the interface between the components illustrated on the test material can be made when test materials involving complex geometry or shapes are tested.

Since the $L_{CR}$ wave travels underneath the surface at bulk, longitudinal wave speed, it will be the first arriving wave at receivers along its path. The change in travel-time of the wave will be indicative of the stress change. The stress induced travel-time changes are small, however, and very accurate and precise methods are required to accomplish this measurement. The following is a description of a suitable data collection method using a high speed digitizing card and an appropriate interface program on a personal computer.

Figure 3:
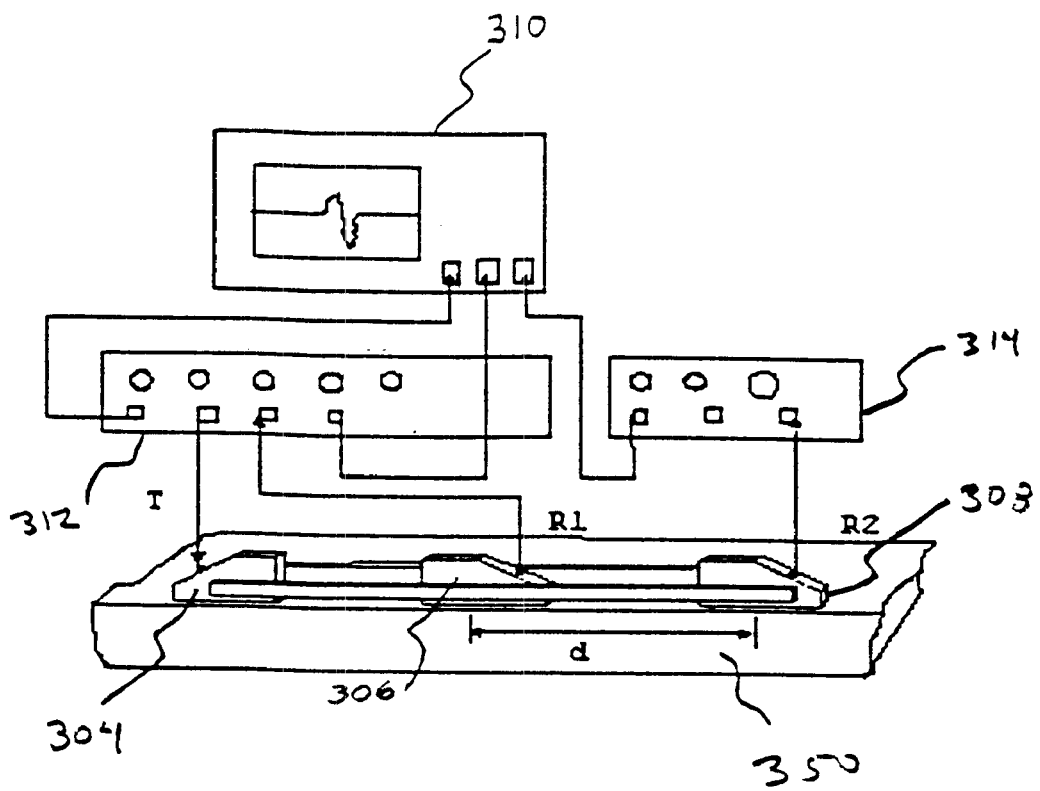

A variety of measurement systems may be used for collecting $L_{CR}$ data. Typical systems include a commercial ultrasonic pulser/receiver as well as an oscilloscope and the $L_{CR}$ transducer, as shown in FIG. 3. The specimen or test sample 350 is again shown in contact with a transducer 304 and two receiving probes 306, 308. Also shown is a computer or oscilloscope 310, the pulser/receiver 312, and a preamp 314. The oscilloscope 310 may be a stand-alone unit, such as LeCroy digital oscilloscope, or a high speed digitizing board (Gage Scope 265) inserted in a personal computer. If the high speed digitizing board is used, the computer 310 must be fitted with suitable software, such as Lab View, so that the travel-time measurements can be made. The instrument must be able to resolve arrival-times in the 0.1 to 0.01 ns range. The pulse originates as the pulser/receiver 312 emits a spike that excites the oblique sending transducer 304. The pulse travels as a $L_{CR}$ wave through a short distance in the material, and is received by the two transducers 306, 308 which are arranged in tandem. In some cases, a preamplifier 314 is inserted in the connection to the second transducer 308 to increase the signal amplitude. For a probe spacing (d) between the first probe 306 and the second probe 308 (or R1 and R2) of 152.4 mm (6 in.), the initial travel time in a stress-free state between the two tandem transducers is about 25.7 $\mu s$. With an instrumentation resolution of 0.1 ns, the system with the probe is capable of measuring travel-time changes of approximately 0.0004%.

The time resolution (precision) of the high-speed digitizing card is a function of the sampling rate. Lab View enables the presentation of a typical oscilloscope screen on the computer monitor. While the presentation is similar to that of an oscilloscope, there are significant differences that need to be discussed.

The parameter START on LabView is analogous to DELAY on a typical oscilloscope or ultrasonic flaw detector. NUMBER represents the expansion of the time base of the display. The larger the positive value in START, the later the start of the display after the trigger. The smaller the NUMBER value, the fewer points displayed, and the greater the time expansion of the time-base (i. e. smaller $\mu s$/div). The SAMPLING RATE represents the firing rate of the card, which is associated with the maximum time resolution of the system. Note that for dual channel operation, the ACTUAL SAMPLING RATE per channel is one-half of the maximum SAMPLE RATE. POINTS (lower, left corner of screen) describes the total number of points displayed on the screen.

Further, higher precision will be achieved when using Lab View if all data are collected in single channel mode, using Channel A. This is due to the fact that in dual channel mode, the higher speed sampling rate is divided between the two channels so that the actual rate is one half of the peak. In single channel mode, the actual sampling rate is the maximum. A higher speed board than the one used here could give satisfactory performance in dual channel mode.

While the invention has been particularly shown and described with reference to the preferred embodiments, it would be understood by those skilled in the art that various changes in form and detail may be made therein without departing from the spirit and scope of the invention.

I claim:

1. A method for measuring the internal stress in a material comprising the steps of:

(a) applying a transducer probe in physical contact with the material;

(b) applying at least one receiving probe in physical contact with the material;

(c) applying a contact force at an interface between said probes and the material, comprising the steps of placing a variable force ram in physical contact with said probes, attaching a load frame to said variable force ram, and securing said load frame to the material;

(d) transmitting a critically refracted longitudinal wave through the material from the transducer probe to the at least one receiving probe; and (e) calculating the internal stress of the material as a function of a travel time from the transducer probe to the at least one receiving probe of the longitudinal wave through the material.

2. The method of claim 1 wherein the force of step (c) is applied equally against said probes.

3. The method of claim 1 wherein the step of securing said load frame to the material comprises attaching at least one magnet to said load frame.

4. The method of claim 1 further comprising the step of measuring the temperature of the material.

5. The method of claim 4 wherein step (e) further comprises: calculating the internal stress of the material as a function of the temperature of the material.

6. A method for measuring the internal stress in a material comprising the steps of:

(a) placing a first and a second receiving probes in forced contact with the material;

(b) applying a contact force at an interface between said probes and the material, comprising the steps of placing a variable force ram in physical contact with said probes, attaching a load frame to said variable force ram, and securing said load frame to the material;

(c) transmitting a critically refracted longitudinal ultrasonic wave through the material;

(d) measuring the wave at the receiving probes; and (e) calculating the internal stress of the material as a function of a travel time of the longitudinal wave between said probes through the material.

7. The method of claim 6 wherein the forced contact comprises applying an equal contact force to both said probes.

8. The method of claim 6 wherein the step of securing said load frame to the material comprises attaching at least one magnet to said load frame.

9. The method of claim 6 wherein the step of securing said load frame to the material comprises using a mechanical constraint.

10. The method of claim 6 wherein the step of securing said load frame to the material comprises using a vacuum constraint.

* * * * *